United States Patent [19]
Gadot

[11] Patent Number: 5,797,881
[45] Date of Patent: Aug. 25, 1998

[54] INTRAVENOUS INFUSION APPARATUS

[76] Inventor: Amir Gadot, 53, Bialik St., Givat Shemuel 51905, Israel

[21] Appl. No.: 736,394

[22] Filed: Oct. 24, 1996

[30] Foreign Application Priority Data

Jun. 20, 1996 [IL] Israel ......................... 118689

[51] Int. Cl.$^6$ ........................................... A61M 37/00
[52] U.S. Cl. ........................ 604/133; 604/131; 604/132; 604/153
[58] Field of Search ..................... 604/131, 132, 604/133, 134, 246, 119, 319, 153; 600/578, 579

[56] References Cited

U.S. PATENT DOCUMENTS

| | | | |
|---|---|---|---|
| 3,151,616 | 10/1964 | Selfon ............................... | 604/131 |
| 4,429,693 | 2/1984 | Blake et al. ........................ | 604/133 |
| 4,583,972 | 4/1986 | Hunter, III et al. ................ | 604/133 |
| 4,981,474 | 1/1991 | Bopp et al. ........................ | 604/133 |
| 5,281,202 | 1/1994 | Weber et al. ...................... | 604/132 |
| 5,342,313 | 8/1994 | Campbell et al. ............... | 604/132 X |
| 5,368,569 | 11/1994 | Sanese .......................... | 604/132 X |

FOREIGN PATENT DOCUMENTS

| | | | |
|---|---|---|---|
| 1013635 | 7/1977 | Canada ............................. | 604/134 |
| 64848 | 1/1982 | Israel . | |

*Primary Examiner*—Kien T. Nguyen
*Assistant Examiner*—Justine R. Yu
*Attorney, Agent, or Firm*—Frishauf, Holtz, Goodman, Langer & Chick

[57] ABSTRACT

An intravenous infusion system is provided comprising (a) a mechanical clamp for expelling intravenous infusion liquids from a bag containing liquids; (b) a hollow tube connected to the mechanical clamp; and (c) a hollow needle connected to the hollow tube capable of being inserted into the vein of a patient requiring an intravenous infusion. The mechanical clamp comprises a pair of superposed members hingedly connected at one end thereof, each of the members normally being curved outwardly from the one end and diverging therefrom when in the normally opened position, the members having cooperating locking portions at the distal end, the members being formed of a rigid but resiliently deformable material, each of the members being divided into a plurality of sections by longitudinally extending slit portions, whereby when the bag is enclosed within the clamp and the locking portions are cooperatively engaged, the curvature of the members is reversed and a positive pressure is applied thereto to thereby expel the liquid from the bag.

12 Claims, 5 Drawing Sheets

INTRAVENOUS INFUSION APPARATUS

The present invention relates to an apparatus designed for expelling an intravenous infusion liquid from a standard plastic infusion bag. The apparatus is particularly useful in all cases where infusion has to be carried out in emergencies outside of a clinic, such as in battle or after an accident. The invention is an improved version of the apparatus invented by the present inventor and Patented in Isreal under : No. 64848.

BACKGROUND OF THE INVENTION

Intravenous infusion solutions are supplied in standard disposable plastic bags. They are conventionally suspended on a stand and the infusion liquid is delivered into the vein or the marrow of the bone of a patient through a hose and injection needle by gravity. In all cases where no stand or any other raised object is available for suspending the bag this has to be held above the patient by medical personnel until it is empty, evidently occupying the person unnecessarily while he or she could help other patients during this period.

In the year 1982 the present inventor conceived a device for squeezing the liquid out of its bag by means of a clamp consisting of two flat resilient plates connected by a hinge at their one end. The bag was configured to be placed between the two plates which then were connected at the end opposite the hinge to compress the bag and to expel the fluid by their elasticity.

This device, however, suffered from several drawbacks:
—The conventional plastic infusion bag is provided with an outlet in the center of one of its short sides and with a support opening for suspending it at its other end. The former device was designed for being placed across the length of the bag and was not suitable for squeezing the entire fluid out through the opening. A second drawback was that closing the two plates at their one end demanded a major effort, since the plates had to be strong enough for the designed task or, if they were too elastic, could not press with sufficient force onto the sides of the bag.

This led the present inventor to design an apparatus or device which has the object of forcefully expelling the entire solution out of the bag into the body of a patient.

Another object is to close the apparatus on the bag while demanding a relatively, small effort, enabling a nurse or other female to carry out an infusion in the open.

It is another object to provide an infusion apparatus of simple design which does not require maintenance or other service, which is easy to operate by unskilled personnel, even if the insertion of an injection needle is initially carried out by a trained medic.

The device according to the present invention should be of light weight permitting the patient to move freely without being tied to a fixed location. And it is a final object to provide an infusion apparatus at low cost which may be disposed after one or after a few uses.

SUMMARY OF THE INVENTION

In accordance with a first aspect the invention comprises a mechanical clamp for expelling intravenous infusion liquid from a standard resilient plastic infusion bag, after having been placed into the clamp. The bag is commonly of rectangular shape and contains a port and spout for connection of a flexible tube at one end and a perforated lug at the other end for suspending the bag on a hook on a stand. The clamp includes two flat, resilient plates of substantially rectangular shape, the length of each plate being slightly larger than the length of the bag, while its width is not less than the width of the bag. The two plates are hingedly interconnected by hinge means at one end, and provided with means for releasably connecting the two plates at their other end, after the bag has been placed between the two plates with the lug end close to the hinge. Thee plates may be fabricated of a resilient plastic material of light metal sheeting.

In order to permit closing of the two plates by using less force after a full bag has been placed between the two, and to prevent breakage, each plate is divided into two or three parallel sections by one or two longitudinal slots starting close to the hinged ends and extending to the free ends. The respective sections are now closed one by one which requires less force than required if the undivided plates are to be closed along their entire width. With the object of providing free access to the spout on the bag a recess is provided in the center of the free edge of each plate.

In a preferred embodiment the hinge is a cylindrical, hollow plastic hinge integral with the two plates.

In another preferred embodiment the two plates forming the clamp are separate and interconnected by a conventional hinge construction including a hinge pin.

In a preferred embodiment the connecting means includes a hook-like portion at the free end of one of the plates extending toward the second plate, configured to enclose the straight end of this second plate. In the case of the plates being divided into parallel sections each section is similarly formed to engage with the corresponding section of the other plate.

A hole is preferably provided in each plate close to the hinged edges for placing a pin through these holes and the hole in the lug of the bag for securing the bag in its position between the two plates. In another embodiment one of the two plates is provided with an aperture, while the other plate exhibits a pin-like, inwardly extending protrusion configured to be inserted into this hole while closing the clamp on the bag.

The two plates may be planar or, even better, curved in outside direction in order to provide stronger pressure onto the bag. The clamp may be provided with a carrying strap enabling a patient to move around during the infusion process.

In a another embodiment, two metallic contact plates of a battery-operated alarm system are inserted juxtaposed to one another on the inside surfaces of the two plates, the contacts being adapted to operate the alarm system, as soon as the infusion bag has been emptied.

DETAILED DESCRIPTION OF THE DRAWINGS

Figure 1:
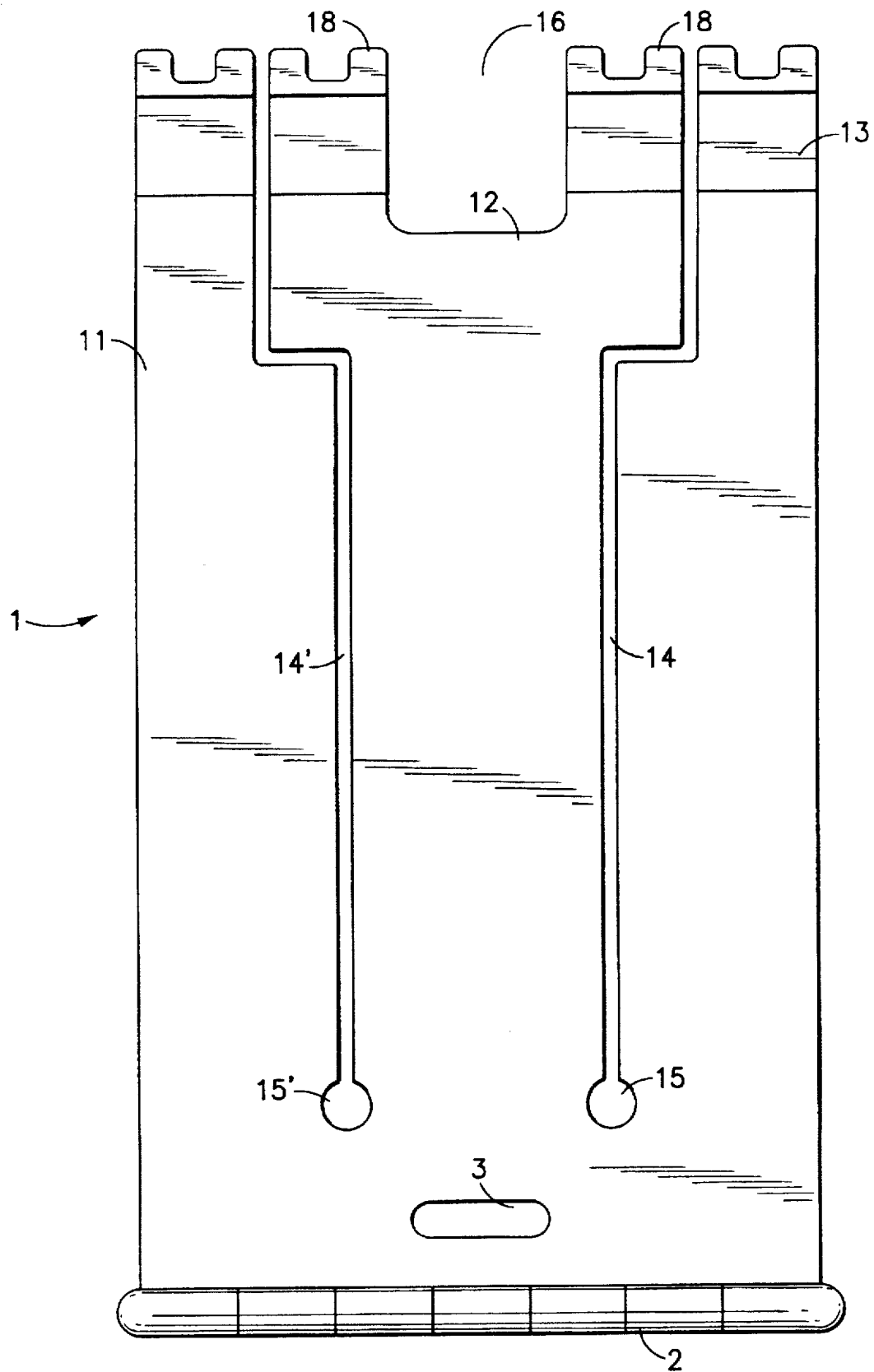
FIG. 1 illustrates one of the plates of the clamp of the invention divided into three sections.
Figure 2:
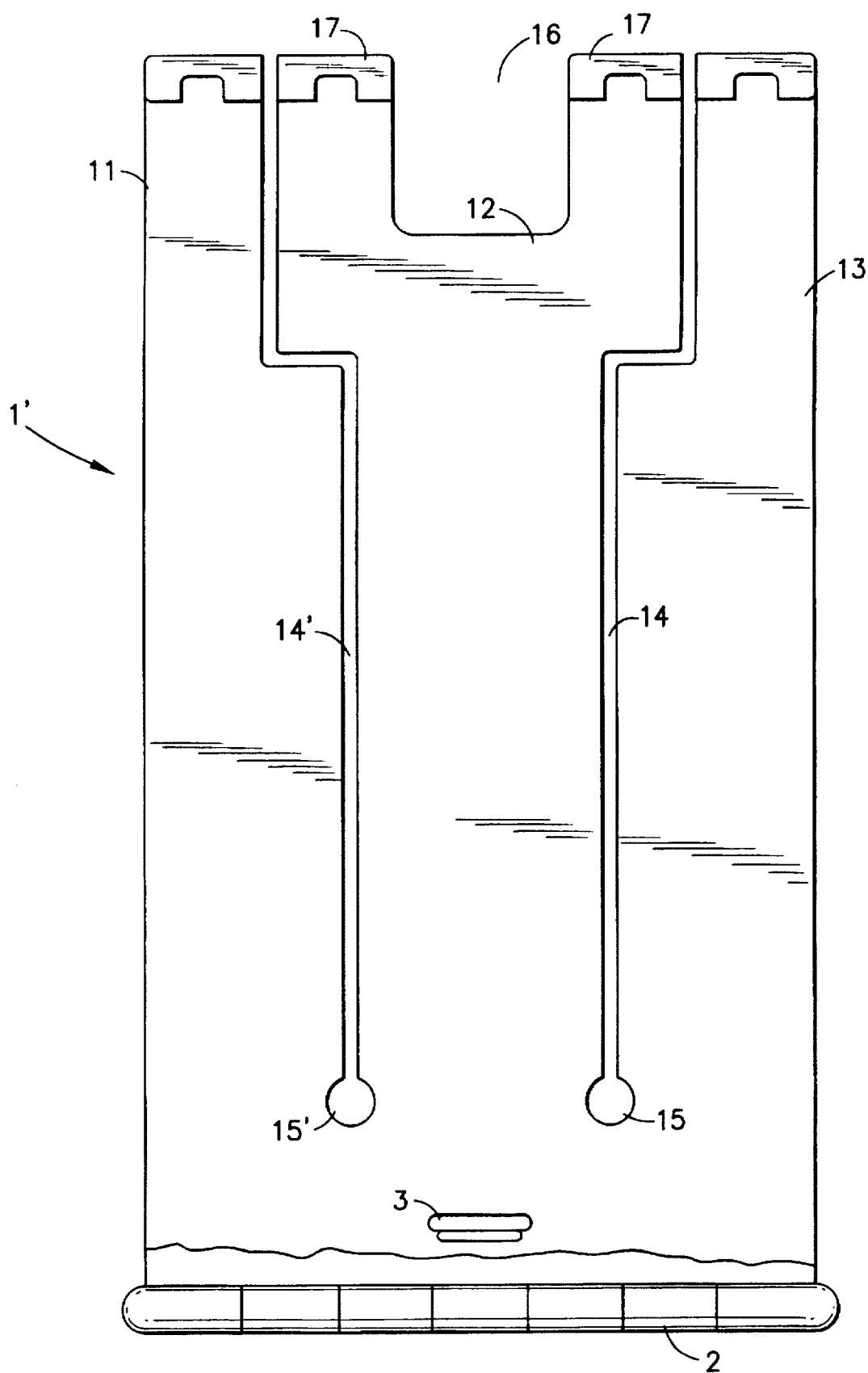
FIG. 2 illustrates the second plate of the clamp.
Figure 4:
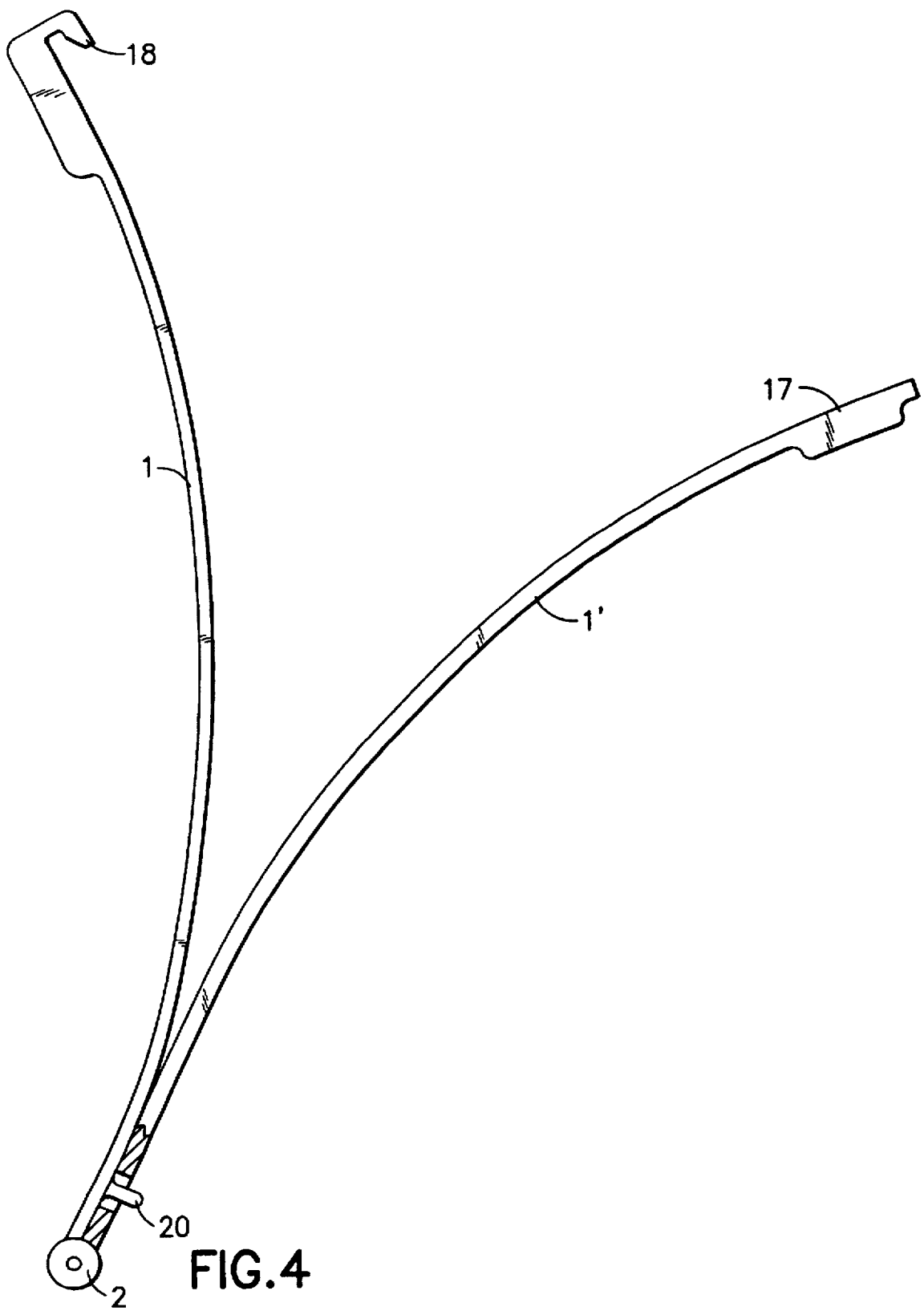
FIG. 4 is a side view of the clamp assembled from the plates shown in FIGS. 1 and 2.

FIGS. 1, 2 and 4 show the clamp of the invention from above and from the side. The clamp includes two outwardly bent plates 1 and 1' of rectangular configuration of a resilient but firm material such as plastic sheeting. As shown in FIG. 4, the two plates are an outwardly direction and are connected at the "lug"-end by a plastic hinge 2. A hole 3 in each plate permits firm securing of the infusion bag by a pin extending through holes 3 and the hole in the bag's lug. The plates are divided into three parallel sections 11, 12 and 1.3 by two slots 14 and 14' which end close to holes 3 in the form of circular apertures 15, 15'. The central sections 12 are recessed by rectangular cut-outs 16 permitting access to the outlet port and spout of the bag. The "port"-ends of the plates are provided with connecting means as follows: The end of plate 1 is divided into teeth with hook-like, inwardly extending locking portions 18 which engage with the straight ends 17 of plate 1. It is understood that the two plates are closed over the bag with each section closed separately, which permits closure with less physical effort.

Figure 3:
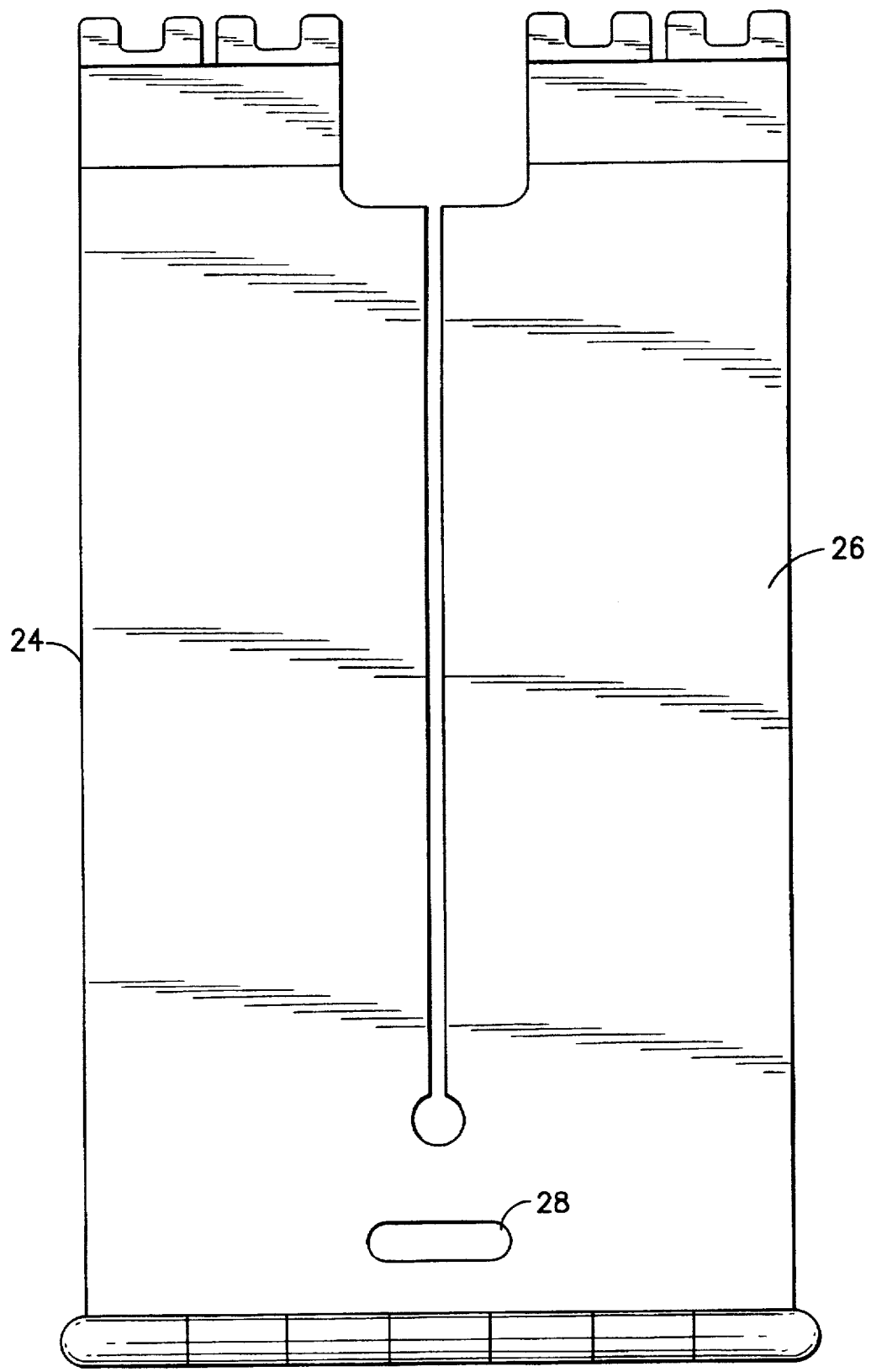
FIG. 3 illustrates, one of the plates of the clamp divided into two sections.

FIG. 3 shows a plate divided into two instead of the three sections shown in the foregoing. Closing of the two portions 24, 26 demands a somewhat stronger effort than with the plates divided into three sections.

Figure 5:
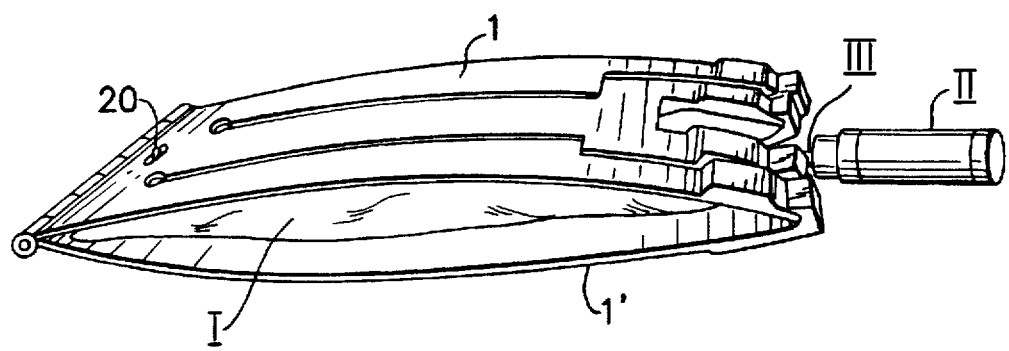
FIG. 5 is an isometric side view of an infusion bag with a syringe attached thereto and enveloped by the clamp of the invention.
Figure 6:
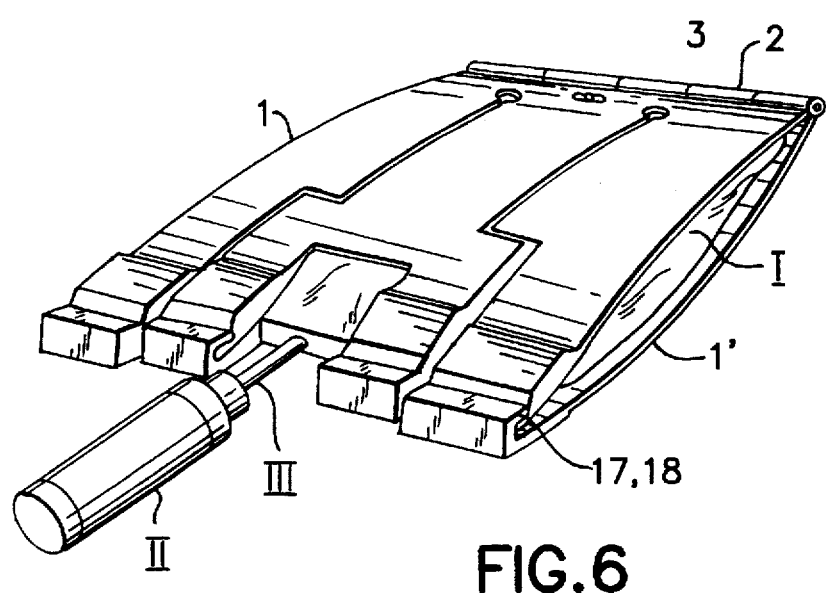
FIG. 6 is a second isometric view of the infusion bag and clamp of FIG. 5.

As shown in FIGS. 4 and 5 the plastic clamp is composed of plates 1 and 1' and envelops an infusion bag I with the long side of the clamp covering the entire length of the bag and extending over its ends. The bag is firmly held in position by a pin 20 pushed through the holes 3 in the plates and the hole in the lug of the bag. The spout of the bag is connected to a syringe II by a flexible hose III. Owing to the outward curvature of the two plates, the clamp exerts a strong pressure on the bag starting from the lug end and squeezes the entire solution out of the bag while compressing it into flatness. The apparatus is to be used in all situations where there is no possibility to suspend the bag from a stand, a post or even a tree, such as in the field of battle, after traffic accidents and the like.

It should be understood that the two plates may be planar instead of curved, with the object of their ready transporting, but with less expelling force. The hinge and the closure may be designed in other ways than disclosed in the foregoing, but the aforedescribed components are preferable owing to their simple design and their relative low cost.

I claim:

1. An intravenous infusion system comprising a mechanical clamp for expelling an infusion liquid from a substantially rectangular, flexible bag containing said liquid, said bag being of a rectangular shape having a length and a width, with the length being greater than the width and having a port and spout for connection of an injection needle by a flexible tube at a first short side thereof and a perforated lug at a second short side thereof, said mechanical clamp comprising a pair of superposed, rectangular plates of a resilient material of a length greater than the length of said bag and of a width substantially co-extensive with the width of said bag in an emptied state of the bag, said plates being connected along first ends thereof by a hinge assembly and being provided along second ends thereof with an operating locking assembly, each of said two plates being divided into at least two sections by at least one longitudinally extending slot, said bag being configured to be placed between said two plates with its lug adjacent to said hinge assembly and with said port and spout adjacent said locking assembly, whereupon by closing said clamp over said bag by said locking assembly, positive pressure is applied to said bag to expel said liquid out through said port to said needle.

2. The infusion system of claim 1, wherein both said plates of said clamp are outwardly curved in an open state of said clamp with their first ends connected by said hinge assembly.

3. The infusion system of claim 1, wherein said locking assembly comprises hook-like portions at the second end of one of said plates and cooperating tongues at the second end of the other plate.

4. The infusion system of claim 1, wherein each of said plates is provided with a perforation close to its first end cooperating with said perforation in said lug of said bag, permitting fixation of said bag in said clamp by a pin pushed through said perforations in said plates and in said lug.

5. The infusion system of claim 1, wherein one of said plates is provided with a perforation close to its first end cooperating with said perforation in said lug of said bag, and wherein the other plate is provided with an inwardly directed pin-like protrusion configured to be passed through said perforation in said lug and through said perforation in said one plate.

6. The infusion system of claim 1, wherein said hinge assembly includes a cylindrical, hollow plastic hinge integral with the first ends of said resilient plates.

7. The infusion system of claim 1, wherein said hinge assembly includes a hinge pin.

8. The infusion system of claim 1, wherein each said plate is divided into two sections by a longitudinal slot starting at said second end of each plate and terminating in the form of a round hole close to said first end.

9. The infusion system of claim 1, wherein each said plate is divided into three sections by two longitudinal slots starting at the second end of each plate and each slot terminating in the form of a round hole close to said first end.

10. The infusion system of claim 1, wherein said plates are made of a plastic resilient material.

11. The infusion system of claim 1, wherein each said plate is provided with a recess in a central portion of its second end, permitting the passage of said flexible tube and access to the spout of said bag.

12. The infusion system of claim 10, wherein two metallic contact plates of a battery-operated alarm system are attached to insides of said two plates in juxtaposed alignment, configured to operate the alarm system when the infusion bag is empty.

* * * * *